US012620261B2

(12) United States Patent (10) Patent No.: US 12,620,261 B2
Matteucci et al. (45) Date of Patent: May 5, 2026

(54) SYSTEM AND METHOD FOR READING AND ANALYSING BEHAVIOUR INCLUDING VERBAL, BODY LANGUAGE AND FACIAL EXPRESSIONS IN ORDER TO DETERMINE A PERSON'S CONGRUENCE

(71) Applicant: Plenium AG, Muri bei Bern (CH)

(72) Inventors: Caroline Matteucci, Muri bei Bern (CH); Joanna Bessert-Nettelbeck, Bern (CH)

( * ) Notice: Subject to any disclaimer, the term of this patent is extended or adjusted under 35 U.S.C. 154(b) by 559 days.

(21) Appl. No.: 17/416,344

(22) PCT Filed: Dec. 20, 2019

(86) PCT No.: PCT/IB2019/061184
    § 371 (c)(1),
    (2) Date: Jun. 18, 2021

(87) PCT Pub. No.: WO2020/128999
    PCT Pub. Date: Jun. 25, 2020

(65) Prior Publication Data
    US 2022/0067353 A1     Mar. 3, 2022

(30) Foreign Application Priority Data
    Dec. 20, 2018     (CH) ..................................... 1571/18

(51) Int. Cl.
    *G06V 20/40*          (2022.01)
    *G06F 18/214*         (2023.01)
    (Continued)

(52) U.S. Cl.
    CPC ............ *G06V 40/20* (2022.01); *G06F 18/214* (2023.01); *G06N 20/00* (2019.01); *G06V 20/46* (2022.01);
    (Continued)

(58) Field of Classification Search
    CPC ........ G06V 10/40; G06V 10/70; G06V 20/46; G06V 20/49; G06V 40/16; G06V 40/174;
    (Continued)

(56) References Cited

U.S. PATENT DOCUMENTS

2004/0107103 A1 *  6/2004  Iyengar et al. ......... G10L 15/25
                                                    704/E21.02
2008/0260212 A1    10/2008  Moskal et al.
                    (Continued)

FOREIGN PATENT DOCUMENTS

CN     104537361 A     4/2015
CN     107578015 A     1/2018
            (Continued)

OTHER PUBLICATIONS

International Search Report & Written Opinion for PCT/IB2019/061184 dated Mar. 20, 2020, 13 pgs.
            (Continued)

*Primary Examiner* — Andrew W Johns
(74) *Attorney, Agent, or Firm* — Kolitch Romano Dascenzo Gates LLP

(57) ABSTRACT

According to the invention, is provided a data processing system for determining congruence or incongruence between the body language and the Speech of a person, comprising a self-learning machine, such as a neutralneural network, arranged for receiving as input a dataset including: approved data of a collection of analysed Speeches of persons, said approved data comprising for each analysed Speech: * a set of video sequences, comprising audio sequences and visual sequences, each audio sequence corresponding to one visual sequence, and * an approved congruence indicator for each of said video sequence—said
            (Continued)

self-learning machine being trained so that the data processing system is able to deliver as output a congruence indicator.

26 Claims, 4 Drawing Sheets

(51) Int. Cl.

| | |
|---|---|
| *G06N 20/00* | (2019.01) |
| *G06V 40/16* | (2022.01) |
| *G06V 40/20* | (2022.01) |
| *G10L 25/63* | (2013.01) |
| *H04N 5/76* | (2006.01) |
| *A61B 5/16* | (2006.01) |

(52) U.S. Cl.
CPC ............ *G06V 20/49* (2022.01); *G06V 40/174* (2022.01); *G10L 25/63* (2013.01); *H04N 5/76* (2013.01); *A61B 5/164* (2013.01); *A61B 5/167* (2013.01)

(58) Field of Classification Search
CPC ..... G06V 40/20; G06F 18/254; G06F 18/256; G06N 20/00; G10L 15/02; G10L 15/08; G10L 2015/226; G10L 2015/227; G10L 25/51; G10L 25/57; G10L 25/63
See application file for complete search history.

(56) References Cited

U.S. PATENT DOCUMENTS

| | | | |
|---|---|---|---|
| 2013/0121591 A1* | 5/2013 | Hill ..................... G10L 15/1815 |
| | | | 382/195 |
| 2013/0139255 A1 | 5/2013 | Tegreene | |
| 2013/0139257 A1 | 5/2013 | Tegreene | |
| 2013/0139258 A1 | 5/2013 | Tegreene | |
| 2013/0139259 A1 | 5/2013 | Tegreene | |
| 2013/0300900 A1 | 11/2013 | Pfister et al. | |
| 2016/0354024 A1 | 12/2016 | Keshava et al. | |
| 2017/0061966 A1* | 3/2017 | Marcheret et al. .... G06V 20/41 |
| 2017/0364741 A1 | 12/2017 | Hau | |
| 2018/0160959 A1 | 6/2018 | Wilde et al. | |

FOREIGN PATENT DOCUMENTS

| | | | |
|---|---|---|---|
| WO | WO-2008/063155 A2 | 5/2008 |
| WO | WO-2008/063527 A2 | 5/2008 |

OTHER PUBLICATIONS

A. Vrij, et al., "Detecting Deceit Via Analysis of Verbal and Nonverbal Behavior", Journal of Nonverbal Behavior, vol. 24, No. 4, 2000, pp. 239-263.
"BATT—Behaviour Analysis Training Tool", presentation by Joanna Bessert-Nettelbeck (Founder), Caroline Matteucci (Co-Founder), 30 pages.
"BATT", presentation by Joanna Bessert-Nettelbeck (Founder), Caroline Matteucci (Co-Founder), 47 pages.

* cited by examiner

SYSTEM AND METHOD FOR READING AND ANALYSING BEHAVIOUR INCLUDING VERBAL, BODY LANGUAGE AND FACIAL EXPRESSIONS IN ORDER TO DETERMINE A PERSON'S CONGRUENCE

RELATED APPLICATIONS

The present application is a national phase of PCT/IB2019/061184, filed Dec. 20, 2019, which claims the benefit of Swiss Patent Application No. CH 01571/18, filed Dec. 20, 2018. The entire disclosures of which are hereby incorporated by reference.

FIELD OF THE INVENTION

The present invention concerns a method and a system for providing indicators of congruence or incongruence between the body language (including all facial expressions) and the Speech of a person. This method and system are useful to provide, by reading and analysing the body language (including all facial expressions) and the features of the Speech, which could be done totally or partially automatically, the congruence of a person's behaviour or Speech in relation to the situation (comfort, part of the 6C of the congruence method: calibration, comfort, context, change, combination, consciousness).

A lot of situations exist where there is a need for establishing the congruence of a Speech of a person. Such a tool would notably be useful and applicable to both the business and legal worlds. For instance, in human resources management (recruitment, conflict management, talent integration, communications, etc.), for all insurances purposes (medical consultant, insurance fraud, etc.), for social services (coaches, psychologists, psychiatrists, telemedicine, etc.) for all justice and/or police departments (police investigation, judge, lawyers, etc.) for security services (migrations, customs, airport, security agent, etc.) and all calls (interviews/conference calls/business calls/telemedicine, etc. supported by a camera).

The fields of use are therefore defined as follows, in a non-limitative way: human resources management (recruitment, conflict management, talent integration, communications, etc.), for all insurances purposes (medical consultant, insurance fraud, etc.), for social services (coaches, psychologists, psychiatrists, telemedicine, etc.) for all justice and/or police departments (police investigation, judge, lawyers, etc.) for security services (migrations, customs, airport, security agent, etc.) and all calls (interviews/conference calls/business calls/telemedicine, etc. supported by a camera).

Such an analysis is part of the personality profiling field in psychology, notably known as an investigative tool used by law enforcement agencies to identify likely suspects. This method and system is taking into account all the bodily and verbal cues necessary for reading and analyse behaviour, making it possible to establish the congruence or incongruence of an individual, namely his/her consistency or non-coherence as well as his behavioural profile.

DESCRIPTION OF RELATED ART

There exist numerous prior art references presenting systems and methods for detecting in a speech of a subject the truth or the deceit. For instance, in US20080260212A1 images of the subject's face are recorded, a mathematical model of a face defined by a set of facial feature locations and textures and a mathematical model of facial behaviours that correlate to truth or deceit are used. The facial feature locations are compared to the image to provide a set of matched facial feature locations and the mathematical model of facial behaviours are compared to the matched facial feature locations in order to provide a deceit indication as a function of the comparison.

Also CN104537361 relates to a lie-detection method based on a video. This lie detection method includes the steps of detecting visual behaviour characteristics of a detected object according to video images, detecting physiological parameter characteristics of the detected object according to the video images, and obtaining lying probability data by combining the visual behaviour characteristics with the physiological parameter characteristics.

WO2008063527 relates to procedures to allow an indication of truth or lie to be deduced, notably (a) monitoring the activation of a plurality of regions of a subject's brain while the subject answers questions and (b) measuring one or more physiological parameters while the subject answers questions, and combining the results of (a) and (b) to form a composite evaluation indicative of the truth or lie in the subject's response.

US2016354024 concerns detection of deception and prediction interviewer accuracy. Physiological information of the interviewer during the interview is recorded by at least a first sensor, including a time series of physiological data. By processing the recorded physiological information, the interview assessment calculated by a computer indicates at least one of whether a statement made by the interviewee is likely to be deceitful and whether the interviewer is likely to be accurate in estimating truthfulness of the interviewee.

WO2008063155 relates to deception detection via functional near-infrared spectroscopy. More precisely, Functional near-infrared (fNIR) neuroimaging is used to detect deception. Oxygenation levels of portions of the brain of a subject are imaged via fNIR spectroscopy and the measured oxygenation levels are utilised to determine if the subject is telling a lie or a truth.

Some other prior art references relate to the detection of hacking in remote communication systems, notably providing deceptive, i.e. untrue or false, information. For instance, US2013139259A1, US2013139257A1 and US2013139255A1 present systems and methods for detecting masking of deceptive indicia in communications content. In such cases, according to one possibility the following steps are implemented: receiving one or more signals associated with communications content provided by a first participant in a communications interaction; and detecting at least one indicia of a modification of the communications content associated with at least one indicia of deception by the first participant.

In CN107578015, a first conception of an identification and feedback system and method is presented, in which, a collecting module is used for collecting video samples, screening out target images from the video samples for data cleaning, marking the data-cleaned target images and computing a first impression numerical value according to marking results; a modelling module is used for detecting facial actions, hand actions and body actions in the video samples and establishing an image characteristic learning model and an integrated learning model according to detecting results. A detecting module is used for identifying a video to be detected through the image characteristic learning model and the integrated learning model; a feedback module is used for analysing results identified by the detecting module according to the first impression numerical value and a present specific task and outputting feedback information for determining the first impression left by a newly met person.

Also, US20080260212 relates to a method for detecting truth or deceit comprising providing a video camera adapted to record images of a subject's face, recording images of the subject's face, providing a mathematical model of a face defined by a set of facial feature locations and textures, providing a mathematical model of facial behaviors that correlate to truth or deceit, comparing the facial feature locations to the image to provide a set of matched facial feature locations, comparing the mathematical model of facial behaviors to the matched facial feature locations, and providing a deceit indication as a function of the comparison. In «Detecting deceit via analysis of verbal and non-verbal behavior», Aldert Vril et al; Journal of Nonverbal behaviour; 1 Dec. 2000 on shows that nonverbal behaviour is useful in the detection of deceit and lies. Another method is described in US20130139258, in which is/are detecting one or more indicia of deception associated with one or more signals associated with communications content provided by the participant in several communications interactions.

None of these technologies allow the detection of congruence or non-congruence in a Speech of a person or giving some indicators of congruence or incongruence between the body language and the Speech of a person. Such indicators of congruence or incongruence would be very useful in a lot of situations for confirming or disconfirming the intuition of the interviewer (or more generally the person who see and listen to the Speech, that can be contained in a video). Moreover, in case of live interviews, such indicators would be a strong help to the interviewer and in charge of the dialogue to decide and apply the appropriate communication strategy in the continuing discussion.

BRIEF SUMMARY OF THE INVENTION

According to the invention, these aims are achieved by means of a method for providing indicators of congruence or incongruence of between the body language (including micro expressions) and the audio part of a Speech of a person comprising the following steps:

a/ providing a video recording device dapted to record images of a subject including face and at least some parts of the body (this video recording device can therefore record a video containing a visual portion=images and/or an audio portion=sound), b/ recording a video of a Speech (or more generally of an oral and physical piece of communication from a person, including the body language) of that person with said video recording device, said video being divided into n video sequences (or n visual sequences) comprising n sequences of images and n corresponding audio sequences, c/ for each sequence of images, detecting at least one Visual cue Vc and attributing at least one rating among positive Vc+, neutral Vc0 or negative Vc− for each visual cue Vc, d/ for each audio sequence, detecting at least one Audio cue Ac and attributing at least one rating among positive Ac+, neutral Ac0 or negative Ac− for each Audio cue Ac, e/ for each video sequence, comparing the rating of said Audio cue Ac with the rating of said Visual cue Vc, and giving a congruence indicator which is a positive congruence indicator if both ratings are either positive (Vc+ and Ac+), negative (Vc− and Ac−) or neutral (Vc0 and Ac0), a negative congruence indicator if one of the ratings is positive and the other one is negative (Vc+ and Ac−, or Vc− and Ac+), or a neutral congruence indicator if one of the ratings is neutral (Vc0 or Ac0).

Depending on the Visual cue Vc (respectively Audio cue Ac), each Visual cue Vc (respectively Audio cue Ac) can be attributed one, or two ratings among positive rating, neutral rating or negative rating, in accordance with the table, as defined below. For instance, a Visual cue Vc, can have two ratings such as Vc+ and Vc− (e.g. see below for Tongue out=VcTo, that has a possibility of a positive and a negative rating). Such a Visual cue Vc also can have a neutral rating Vc0.

According to the invention, these aims are also achieved by means of a system for providing indicators of congruence or incongruence between the body language and the Speech of a person, comprising a self-learning machine arranged for receiving as input, on the one hand, several sets of audio sequences of a Speech of a person, each audio sequence corresponding to one Audio cue Ac, and, on the other hand, a set of sequences of images of said person during said Speech, said images comprising face and at least some parts of the body. Each of those sequence of images corresponding to one Visual cue Vc, said self-learning machine being trained so that said system is able to deliver as output, after analysing a video sequence comprising one sequence of images and the one corresponding audio sequence, both at least one identified Visual cue Vc based on said sequence of images and at least one identified Audio cue Ac based on said audio sequence, which forms a pair or a group of identified cues (Vc+Ac) leading to the conclusion of said congruence or incongruence.

This allows the system according to the invention, learning by training, of:

recognition and detection of macro and micro expressions (Visual cues), and/or recognition and detection of Non-verbal (whole body) language and proxemics, and/or recognition and detection of comfort, pacificator and discomfort and also asymmetry, and/or recognition and detection of verbal language (such as linguistic, inquire, words, count), enquire and voice (such as rhythm, speed, volume pitch and ton), (Audio cues), and/or recognition and detection of emotions, either through Visual cues (notably macro-expressions, micro-expressions, visual stress signs, visual comfort signs, visual discomfort signs, visual pacificator sign) or through Audio Cues (notably emotional voice (negative or positive); Verbal style: Linguistics, Inquiry, Word, Count, change of verbal style, the sentiment expressed in the audio sequence (positive or negative sentiment), an audio sign of discomfort, an audio sign of comfort and an audio pacificator sign).

A micro expression is an involuntary, transient facial expression of an intense, concealed, emotion that appears on a person's face according to the emotions being experienced. Furthermore a micro expression is the result of the conflict between an innate, involuntary emotional response and the voluntary one. This occurs when the amygdala (the emotion centre of the brain) responds appropriately to the stimuli that the individual experiences but the individual wishes to conceal this specific emotion. This results in the individual very briefly displaying their true emotions followed by a altered emotional display (that can differ from the prior experienced emotion). Human facial expressions of emotions are an unconscious bio-psycho-social reaction that derives from the amygdala and they typically last 0.5-4.0 seconds. A micro expression will typically last a few tenths of a second. Unlike regular facial expressions, micro expressions are very difficult to conceal or control. Micro expressions happen in a fraction of a second (about ⅕ second), but it is possible to capture someone's expressions with a high-speed camera to replay them at much slower speed. There are seven micro expressions that are universal, derived from the five basic emotions (anger, fear, disgust, enjoyment, sadness), those seven are: disgust, anger, fear, sadness, happiness, contempt, and surprise. In addition, the face can express a macro expression showing discomfort, such as lip corners that are completely pulled down and lips tightened and that lasts for more than ⅕ of a second. In the same way, the face, which is called the canvas of emotions, shows the emotions felt by the person. This can be, as said, macro-expressions, micro-expressions, stress, comfort, discomfort etc.

Some techniques have already been developed to detect human facial micro expressions automatically by a video analysis system, such as shown and described in US2013300900 or in US2017364741.

Body language is a type of nonverbal communication in which physical behaviour, as opposed to words, is used to express or convey information. Such behaviour includes emotions that we identify through facial expressions (macro and micro expressions), body posture, gestures or motions, that can reflect comfort, discomfort and pacifying gestures, eye movement (pupils, blinking eyelids, jerking, etc.), touch and the use of space (proxemics). Body language exists in both animals and humans, but this document focuses on human body language. It is also known as kinesics.

The self-learning machine is trained with video sequences resulting from video sequences recording the Speeches and body language (including all facial expressions) of different persons, so that the self-learning machine is to get used to a very large panel of Speech and body language parameters (including Visual cues Vc, and Audio cues Ac).

The self-learning machine is also trained through video sequences where participants watched an "emotionally strong" film in order to produce easily emotions on them, with both macro expressions and micro expressions.

In order to collect and provide the input dataset including approved data of a collection of analysed Speeches of different persons, specialists in profiling (profilers) manually quote the video sequences of a great number of videos of Speeches. More precisely this step of video annotation by profilers allows to give a collection of video sequences (collecting step S1 in FIGS. 1 and 2), therefore a collection of visual sequences and of audio sequences, with each sequence linked to one or more cue from verbal language or from non-verbal language as explained hereinafter. This input data set is used to train the self-learning machine which will be able afterwards to apply the method according to the invention for providing indicators of congruence or incongruence between the body language and the Speech of a person.

The word congruence (congruency or coherence), with respect to body language, refers to the extent to which a person's body language cues correspond to each other in their meaning. In general, our brain synchronises facial expressions, posture, movement and tone of voice. If they remain synchronised with each other, the intended message is transmitted more precisely, efficiently and correctly. If the opposite occurs, it reduces the impact and demonstrates incongruence (incongruency or inconsistency). In this case, congruence (congruency or coherence) or incongruence (incongruency or inconsistency) refers to the relationship between the verbal and non-verbal components as well as a verbal or emblematic lapsus could express a incongruence in itself, of a message.

The communication of the person during his/her Speech is congruent (coherent) if both channels (verbal and non-verbal) agree and are in line with each other. Consequently, a Speech is not congruent (incongruent or incoherent) if both channels (verbal and non-verbal) disagree and are not in line with each other. In order to establish a diagnostic about the coherence or incoherence of the Speech of a person, indicators of congruence or incongruence between the body language and the Speech are established according to the invention. These indicators of congruence or incongruence will allow to provide information about the congruence of a person's Speech and body language, more generally of an oral and physical piece of communication of a person.

It is also possible to detect incongruency in a single channel, namely either through verbal language or through non-verbal language. For instance when two opposite emotions, appearing at the same time on the face (Visual cue); such as anger and joy (this is called chilarity), this is a typical case for detecting incongruency only through non-verbal language. According to another example for verbal language, in audio (Audio cue) when someone says he(she) is very happy, but the energy of his(her) voice is low and the tone low, this is a typical case for detecting incongruency only through verbal language.

In summary, there is:

Congruence (consistency/congruency): when verbal language (Ac=Audio cue) corresponds to non-verbal language (Vc=Visual cue), i.e. in the following cases:

Negative verbal (negative Audio cue Ac−) and negative non-verbal (negative Visual cue Vc−), Neutral verbal (neutral Audio cue Ac0) and neutral non-verbal (neutral Visual cue Vc0), Positive verbal (positive Audio cue Ac−) and Positive non-verbal (positive Visual cue Vc+)

and

Incongruence (Inconsistency/incongruency):

1) As a combination: when verbal language (Ac=Audio cue) does not correspond to non-verbal language (Vc=Visual cue). For example:

Positive verbal (Ac+) and Neutral or negative non-verbal (Vc0 or Vc−),

Neutral verbal (Ac0) and Positive or negative non-verbal (Vc+ or Vc−)

Negative report (Ac−) and Positive or neutral non-verbal (Vc+ or Vc0)

The timing between voice and gestures, . . . etc.

2) And in a single cue: as for example:

a lapsus:

Verbal lapsus

Emblematic lapsus.

any asymmetry of the body (including asymmetry of the face expression); and which outside the Baseline can be considered incongruent.

It is also possible that in the same cue an inconsistency occurs as an emblematic slip for example (Vc−; incongruent). An incongruence can therefore also be established in a single cue (see verbal lapsus or emblematic lapsus).

Also the detection of any single or both audio signal(s) and visual signal(s) of comfort and/or discomfort is important for establishing congruency or incongruency.

The timing between the verbal and the body language is important and crucial since the emotion is felt instantly and not delayed. Therefore, a delayed expression, body language or emblem is sign of an incongruence.

For example, there is an incongruence if a facial expression of happiness (Vc+) is detected as a non-verbal cue (Visual cue) while a verbal cue (Audio cue) states a sentiment of sadness (Ac−). According to another example, there is an incongruence if a facial expression of sadness (Vc−) is detected as a non-verbal cue (Visual cue) while a verbal cue (Audio cue) states a sentiment of happiness (Ac+), for instance when the audio sequence is "I am happy to see you" (positive Audio Cue Ac+) and when in the corresponding Visual sequence are detected dilated nostrils (negative Visual Cue Vc−). As another example, there is an incongruence if a moving back gesture (Vc−) is detected as non-verbal cue (Visual cue) with a positive emotional vocal cue (Audio cue Ac+), these two cues being not consistent.

In the present text, the term "Speech" means an oral and physical piece of expression/communication of a person and covers all such as discourse or discussion taking place from one person or between two or more persons (including an interview between said person or subject and an interviewer) or during an address or a conference, and any other orally expressed communication. The term "Speech" includes therefore the audio or oral part of that piece of communication. The term "Speech" includes also the body language and facial expression of the person in that moment.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figures 1, 2:
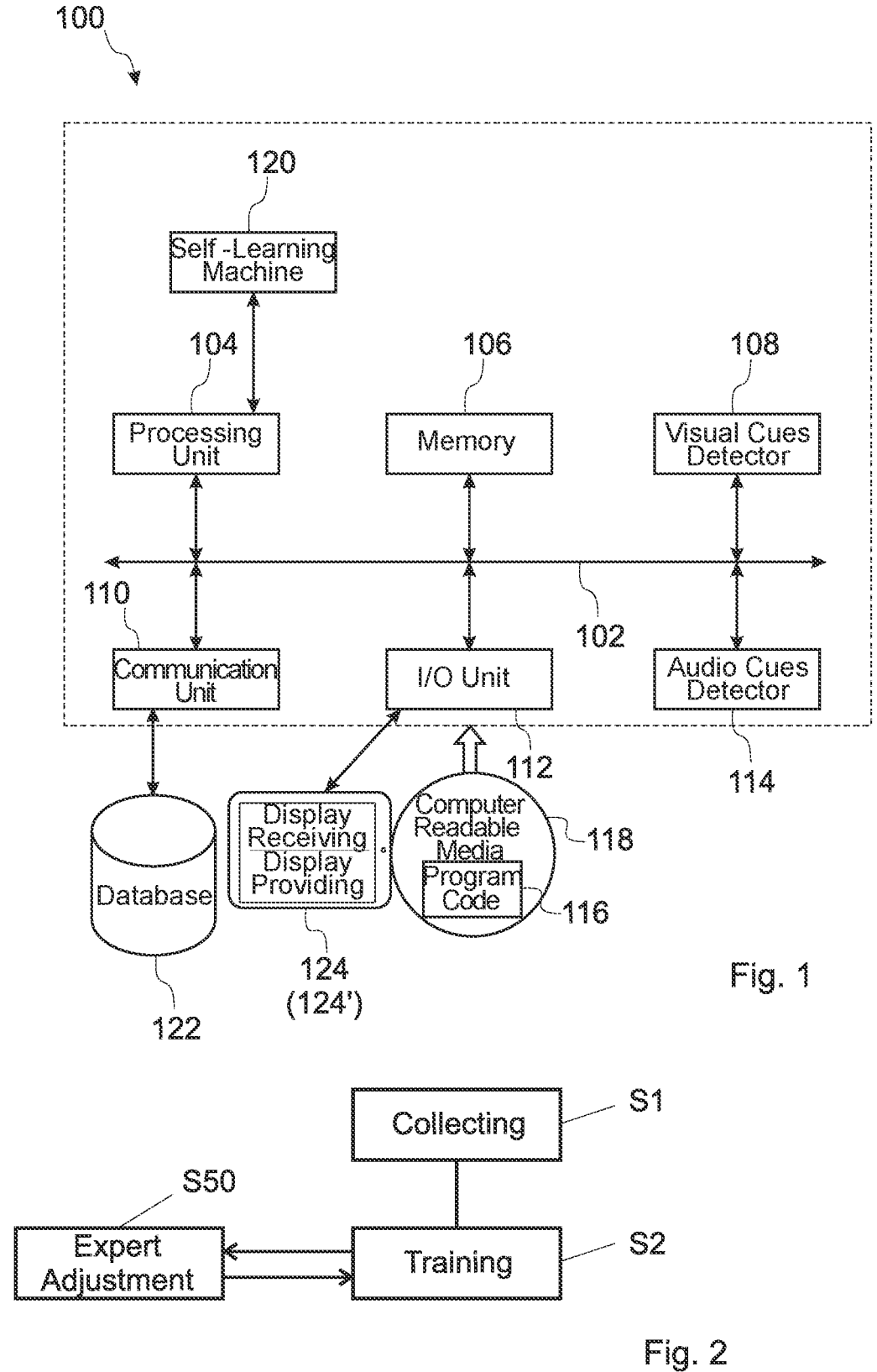
FIG. 1 shows a view of an embodiment of a system according to the present invention, with a data processing system.
FIG. 2 shows a flow-chart representation of a training method which can be implemented in an embodiment of the system according to the present invention.

Visual and Audio cues are separated in two categories, the first category being the baseline (annotated and starting with a B in the table below), namely established as remarkable Visual cues and Audio cues for the person as a neutral state of a person or idiosyncrasy in the specific recorded situation, that includes the calibration of the Visual cues (Vc) and Audio cues (Ac), as well as possible tics, also recognised as a possible medical condition. The second category being said cues (respectively Visual cues Vc and Audio cues Ac), enabling the analysis and establishment of a change in behaviour.

Said Baseline is set first, for example by a visualisation of a reference film by the person/subject. In such an embodiment, the method comprises, before step b), a preliminary step b0) for the baseline establishment during the following, sub-steps are implemented:

i) a reference film is shown to said person, said reference film comprising m reference film sequences, at least some of the reference film sequences being emotionally charged;

ii) during the showing of the film, a recording of a reference video of the person is done;

iii) dividing the reference video into m reference video sequences, each reference video sequence corresponds to a reference film sequence of said film;

iv) for each reference video sequence, detecting at least one Visual cue Vc of a facial expression that is memorised in a baseline table of said person.

Such a reference film is used so that the system according to the invention, via the self-learning machine, learns how to define a Baseline. In another embodiment, this reference film is not required, notably when the self-learning machine is able to calibrate itself to differentiate the Visual cues Vc of the baseline of a person from other Visual cues which are resulting from the emotions of that person during a Speech to be analysed.

In an embodiment, said Visual cue Vc is one of the following: a micro expression VcMe or a body language behaviour (like VcDp; dilated pupils)).

In an embodiment, said micro expression VcMe is one of the following: happiness VcMeH, anger VcMeA, sadness VcMeSa, disgust VcMeD, contempt VcMeC, surprise VcMeS, and fear VcMeF.

In an embodiment, said body language behaviour (cue) is one of the following: a facial expression of the eyes, of the lips, of the nose, motion of the hands or of the fingers on the body with possibly. a position of contact, change of orientation of the body and motion of the feet, of the legs or of the whole body.

Facial expressions include any movement of the facial muscles of more than $1/15$ of a second (macro expressions). Body Language: any movement or posture of the body being either the arms, head, legs, torso, feet, hands between them or resting on top of each other, etc., and any illustrators and emblems. Any change in direction that expresses one of the reactions of our survival instincts system identifiable among others, through the 3 F's (freeze, flee, fight). All comfort gestures, pacifying gesture or discomfort gestures caused by the limbic system and the ANS (autonomic nervous system. Indeed, limbic reactions are instantaneous, experienced, honest, reliable and apply to all of us. These are innate reactions.)

Also, the visual cues deriving from the body language of the person can be used alone or in combination to the audio cues for establishing the rating of this Audio cue Ac (body impact). For instance, some movements of the body, such as the gestures of the arms accompanying a speech (illustrators) increase the person's impact. We are talking about emphasis or isopraxia. In the same way, using the same words as the other person during a discussion increases the impact. This is called mirroring.

In an embodiment, said Audio cue Ac is one of the following: for the voice: Rhythm (pause), Speed (change of speed), Volume (high or low), Pitch, Ton (low or high) and also the emotional voice (negative, positive); Verbal style: Linguistics, Inquiry, Word, Count, for example change of verbal style.

In an embodiment, a reference table is provided with the rating correspondence(s) of the Visual cue Vc and of the Audio cue Ac, used for rating the identified (detected) Audio cue Ac (or Audio cues) of the audio sequence(s), and for rating the identified (detected) Video cue Vc (or Video cues) of the video sequence(s).

In an embodiment, said self-learning machine further receives as input a reference table with the rating correspondence of each of the Visual cues Vc and of each of the Audio cues Ac, and wherein based on said identified Visual cue Vc and on said identified Audio cue Ac of the analysed video sequence and based on said reference table, said system is further able to deliver as output both at least one Visual cue Vc rating and at least one Audio cue Ac rating, which forms a pair or a group of cue ratings. Such a pair or group of cue ratings allows pointing to congruence or to incongruence.

In some cases, this indication of congruence or of incongruence can be considered as an information about the credibility rate of the person whose speech has been analysed according to the invention.

In an embodiment, the table reference is a follows.

TABLE 1

Table of reference : Corresponding ratings for Visual cues
Vc and Audio cues Ac

| Category | Designation of the cue | Abbreviation | Rating of the cue positive (+) or negative (−) |
|---|---|---|---|
| Visual Cue (Vc, non-verbal) Baseline (BVc) | | | |
| | Illustrators (I) | BVcI | |
| | Tics (T) | BVcT | |
| | Motoric disability or medical condition (M) | BVcM | |
| Changes Micro expression (Me) | | | |
| | Happiness (H) | VcMeH | Vc+ |
| | Anger (A) | VcMeA | Vc |
| | Sadness (Sa) | VcMeSa | Vc− |
| | Disgust (D) | VcMeD | Vc− |
| | Contempt (C) | VcMeC | Vc− &/or Vc+ |
| | Surprise (S) | VcMeS | Vc− &/or Vc+ |
| | Fear (F) | VcMeF | Vc− |
| GESTURE | | | |
| Eyes | | | |
| | Dilated pupils (Dp) | VcDp | Vc+ |
| | Contracted pupils (Cp) | VcCp | Vc− |
| | Axis change (Ac) | VcAc | Vc− |
| | Long closure (Lc) | VcLc | Vc− &/or Vc+ |
| | Eyes down (Ed) | VcEd | Vc− |
| Mouth | | | |
| | Tight lips (Tl) | VcTl | Vc− |
| | Tongue out (To) | VcTo | Vc− &/or Vc+ |
| | Tongue presses into the mouth (Tm) | VcTm | Vc− &/or Vc+ |
| Nose | | | |
| | Dilated nostrils (Dn) | VcDn | Vc− |
| Motion (M) of hands or fingers | | | |

TABLE 1-continued

Table of reference : Corresponding ratings for Visual cues
Vc and Audio cues Ac

| Category | Designation of the cue | Abbreviation | Rating of the cue positive (+) or negative (−) |
|---|---|---|---|
| on: | | | |
| | Chin (Chi) | VcMChi | Vc− |
| | Cheek (Che) | VcMChe | Vc− |
| | Mouth (M) | VcMM | Vc− |
| | Hair (H) | VcMH | Vc− &/or Vc+ |
| | Eyes (E) | VcME | Vc− |
| | Nose (No) | VcMNo | Vc− |
| | Finger on forehead (Ff) | VcMFf | Vc− &/or Vc+ |
| | On the sternal supra (Adam's apple) (S) | VcMS | Vc− |
| | Nape (Na) | VcMNa | Vc− |
| | Neck (Ne) | VcMNe | Vc− |
| | Shoulder shrunk (Ss) | VcMSs | Vc− |
| | Body forwards (Bf) | VcMBf | Vc− &/or Vc+ |
| | Hands on hands (Hh) | VcMHh | Vc− &/or Vc+ |
| | Hands on fingers (Hf) | VcMHf | Vc− &/or Vc+ |
| | Hands on forearm (Ha) | VcMHa | Vc− &/or Vc+ |
| | Hands on stomach (Hst) | VcMHst | Vc− |
| | Freeze of the gesture (F) | VcMF | Vc− |
| | Self-hug (Sh) | VcMSh | Vc− &/or Vc+ |
| | Hands on thigh (Ht) | VcMHt | Vc− &/or Vc+ |
| | Head shake negativ (Hsn) | VcMHsn | Vc− |
| | Finger on chest (Fc) | VcMFc | Vc+ |
| | Hands on chest (Hc) | VcMHc | Vc+ |
| Motion (M) with axis change | | | |
| | Ventral denial (Vd) | VcMVd | Vc− |
| | Body backward (Bb) | VcMBb | Vc− |
| | Whole body forward: Territorial invasion (Ti) | VcMTi | Vc− |
| Motion (M) of the feet (F) | | | |
| | Feet wrapped around chair (Fw) | VcMFw | Vc− |
| | Feet backwards (Fb) | VcMFb | Vc− |
| | Feet forward (Ff) | VcMFf | Vc− &/or Vc+ |
| | Only one foot in open position (Fo) | VcMFo | Vc− &/or Vc+ |
| Motion (M) of the Legs (L) | | | |
| | Spread (s) | VcMLs | Vc− &/or Vc+ |
| | Join (j) | VcMLj | Vc− &/or Vc+ |
| | Crossing motion (c) | VcMLc | Vc− &/or Vc+ |
| Illustrators (I) | None (n) | VcPn | Vc− &/or Vc+ |
| | Few (f) | VcPf | Vc− &/or Vc+ |
| | Change (c) | VcPc | Vc− |
| Emblem ( E ) | Misplaced (m) | VcEm | Vc− |
| Audio Cues (Ac, verbal) | | | |
| Baseline voice (BAcV) | | | |
| | Strong (st) | BAcVst | |
| | Soft (so) | BAcVso | |
| Speed: | slow (ss) | BACVss | |
| | fast (sf) | BAcVsf | |
| Volume: | high (vh) | BAcVvh | |
| | low (vl) | BAcVvl | |

TABLE 1-continued

Table of reference : Corresponding ratings for Visual cues
Vc and Audio cues Ac

| Category | Designation of the cue | Abbreviation | Rating of the cue positive (+) or negative (−) |
|---|---|---|---|
| Pitch: | high (ph) | BAcVph | |
| | low (pl) | BAcVpl | |
| Rhythm: | Pause (p) | BAcVp | |
| | No pause (np) | BAcVnp | |
| Baseline verbal style (BAcVs) | | | |
| Linguistics (I) | Spontaneous (s) | BAcVsls | |
| | Reflected (r) | BAcVslr | |
| | Words (w) | BAcVsw | |
| | Inquiry, details given (d) | BAcVsd | |
| | Count (c) | BACVsc | |
| Changes | | | |
| Voice style cues (Vs) | | | |
| Linguistics (L) | More spontaneous (s) | AcVsLs | Ac+ |
| | More reflected (r) | AcVsLr | Ac− |
| Inquiry, details (D) | More details (m) | AcVsDm | Ac− &/or + |
| | Less details (l) | AcVsDl | Ac− &/or+ |
| | Wording (W) | AcVsW | Ac− |
| Count (C) | More (m) | AcVsCm | Ac− |
| | Less (l) | AcVsCl | Ac− &/or + |
| Word (W) | Type (t) | AcVsWt | Ac− &/or + |
| | Change(c) | AcVsWc | Ac− &/or + |
| | Lapsus (l) | AcVsWl | Ac− |
| Voice tone cues (Vt) | | | |
| | Higher pitch (Hp) | AcVtHp | Ac− |
| | Lower pitch (Lp) | AcVtLp | Ac+ |
| | Strong (S) | AcVtSt | Ac− |
| | Soft (So) | AcVtSo | Ac+ |
| Voice speed cues (Vs) | | | |
| | Faster (F) | AcVsF | Ac− &/or + |
| | Slower (S) | AcVsS | Ac− &/or + |
| | More pauses (Mp) | AcVsMp | Ac− |
| Emotional (E) | | | |
| | Positive feeling (p) | AcEp | Ac+ |
| | Negative feeling (n) | AcEn | Ac− |
| | Neutral feeling (0) | AcEO | Ac− &/or + |

This table is non exhaustive and is an exemplary table of the cues which are currently possibly used, but the self-learning machine is able to highlight and detect others visual and/or audio cues.

According to the training method of a self-learning machine 120, in Step S1 is collected an approved dataset of a collection of analysed Speeches of persons, which is provided in step S2 to the self-learning machine 120 for training this self-learning machine. The collection of this approved dataset during step S1 results from:

video recordings of a great number of Speeches of different persons, dividing each Speech into n video sequences comprising n sequences of images (or n visual sequences) and n corresponding audio sequences, and annotating each video sequences by specialists in profiling (profilers) who manually quote the video sequences with at least one Audio cue Ac and at least one Video cue Vc, each cue being attributing by the specialist at least one rating among positive (+), neutral (0) or negative (−).

During the training step S2, in addition to the training of the self-learning machine 120 with the input data set which is completed and renewed regularly, there could be in some cases further interaction with an expert 134 or specialist in profiling, wherein via step S50 there is an expert adjustment of the training of the self-learning machine 120, which correspond to the verification and possible correction by this expert 134 of the quotation of any of the video sequence or any of the audio sequence respectively by at least one corrected Audio Cue Ac or at least one Video Cue Vc.

At that stage, it is to be noted that the "person" means any person independently of the situation and scenario of the Speech, namely any speaker, including but not limited to a lonely speaker, an interviewee or an interviewer (case of a Speech between two or more than two persons with the interviewer being the leading speaker), a speaker during a staff meeting, a speaker during a negotiation meeting, a speaker during a coaching session, an online learning session . . . independently of the number of participants and of the number of speakers present during the Speech. In that respect, the system and the methods presented in the present text can be used mutatis mutandis for one person/speaker only or for two persons/speakers or for more than two persons/speakers, including for all the/speakers participating to the Speech. These remarks are valid for the whole text, and in all paragraphs the term "person" can be used for designing any speaker of the Speech including for instance, but not limited to, a lonely speaker, an interviewee or an interviewer, a speaker during a staff meeting, a speaker during a negotiation meeting, a speaker during a coaching session, an online learning session . . . . In the same way, when presenting in the following text the method and the system applied for a Speech between an interviewee and an interviewer, the same explanations applied in any other case of discussion between two persons or between more than two persons, which means that in the present text "interviewee" can be replaced by "person" and "interviewer" can be replaced by "another person".

Figure 3:
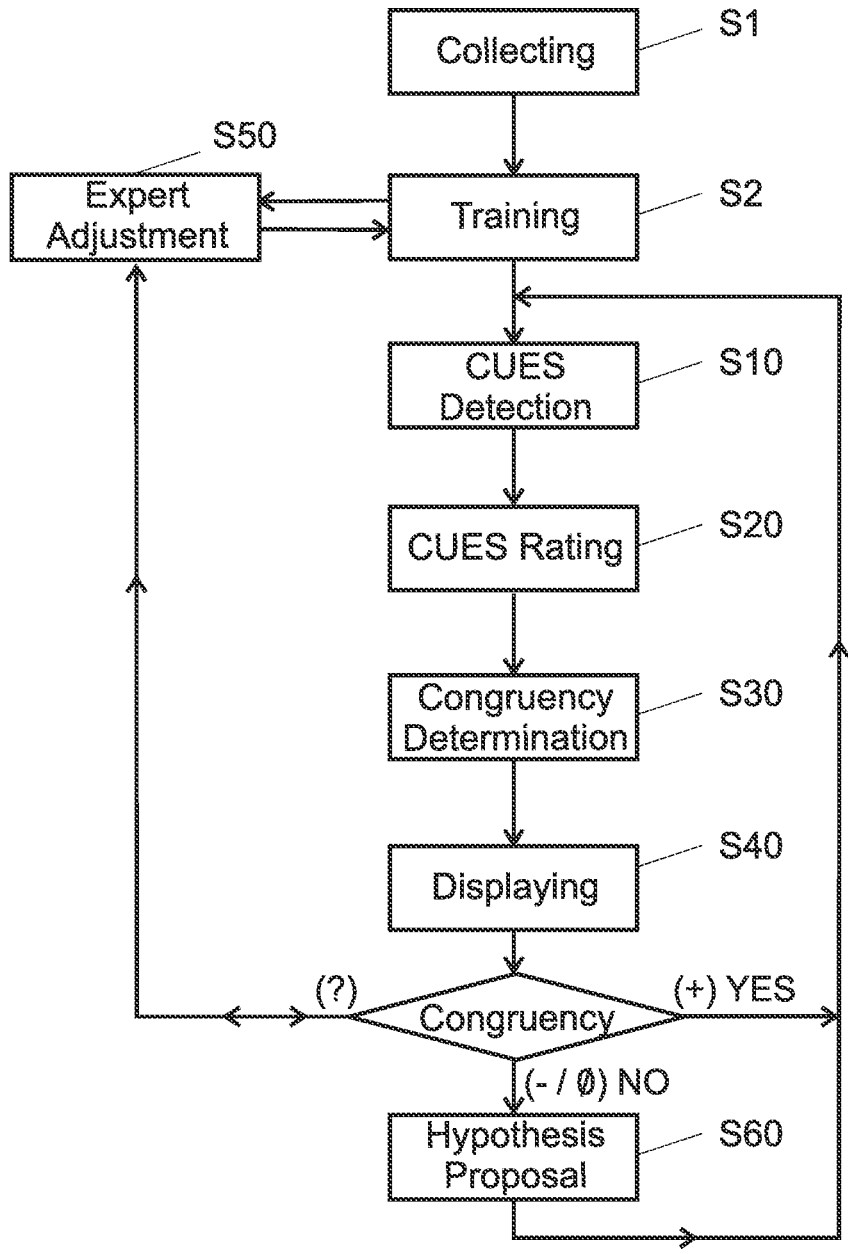
FIG. 3 shows a flow-chart representation of a method for providing indicators of congruence or incongruence between the body language and the Speech of a person which can be implemented in an embodiment of the system according to the present invention.

Relating to FIG. 3 are shown possible steps S10 to S30, or steps S10 to S40, or steps S10 to S50, or steps S10 to S60, of methods for providing indicators of congruence or incongruence between the body language and the Speech of a person which can be implemented in an embodiment of the system according to the present invention.

The initial steps for training the self-learning machine have already been described, namely the collecting step S1 and the training step S2.

Then, before step S10, a video of a Speech of the person (for instance the interviewee 130) is captured, and said video is divided into n video sequences comprising n sequences of images (or n visual sequences) and n corresponding audio sequences.

Then, in step S10, the system performs cues detection, namely for each sequence of images, at least one Visual cue Vc is detected and for each audio sequence, at least one Audio cue Ac is detected.

Then, in step S20, the system performs cues rating, i.e. the system attributes at least one rating among positive Ac+, neutral Ac0 or negative Ac− for each Audio cue Ac and the system attributes at least one rating among positive Vc+, neutral Vc0 or negative Vc− for each visual cue Vc.

Then, in step S30, the system performs congruency determination, which means comparing the rating of said Audio cue Ac with the rating of said Visual cue Vc, and giving a congruence indicator which is a positive congruence indicator if both ratings are either positive (Vc+ and Ac+) or negative (Vc+ and Ac+), a negative congruence indicator if one of the ratings is positive and the other one is negative (Vc+ and Ac−, or Vc− and Ac+), and a neutral congruence indicator if one of the ratings is neutral (Vc0 or Ac0). These steps S10 to S30 are the minimum steps of the method according to the invention for determining congruence in the speech of a person, in the form of a congruence indicator. Then, optionally, in step S40 the system displays a sign representative of the congruence indicator previously established (for instance a displayed sign on display 124 such as "+", "−" or "0" and/or the displaying of an icon and/or the displaying of a colour on a screen (for instance red for a negative congruence indicator, orange for a neutral congruence indicator, green for a positive congruence indicator) and/or the display of a sound in an earpiece of the interviewer 132.

Then, optionally, there are further steps depending of the congruence indicator, each route being independent of the other routes, namely can intervene alone or in combination with one or two of the other routes:

Route 1 (on the right on FIG. 3): if the congruence indicator is positive (+), then the method/system makes a loop back to step S10 in order to evaluate the congruence or incongruence of the Speech of the person (for instance the interviewee 130) for another video sequence;

Route 2 (on the bottom on FIG. 3): if the congruence indicator is negative (−) or if the congruence indicator is neutral (0), then, in step S60 the system displays a list of hypothesis (hypotheses proposal in the form of a list of affirmations and/or of questions) based on said indicator of congruence or of incongruence of the previously analysed video sequence, eventually on the corrected indicator of congruence. When the person is an interviewee 130, another person participating to the Speech, for instance the interviewer 132, can use this list of hypotheses and choose one question or one affirmation among this list to pursue the Speech when in the form of a discussion or an interview between two persons, notably between an interviewee 130 and an interviewer 132. In this case, after one of this hypothesis is used by the other person (the interviewer 132) during the Speech, the method makes a loop back to step S10 in order to re-evaluate the congruence or incongruence of the Speech of the person (interviewee 130) for another video sequence, which congruence indicator is evaluated again in step S30.

Route 3 (on the left on FIG. 3): if the congruence indicator is not clearly established (see "(?)" on FIG. 3), then in step S50 there is an expert adjustment, which correspond to the verification and possible correction by an expert 134 of the congruence indicator, which further step of congruence indicator also possibly serves to train further the self-learning machine 120. Then, the method follows previously described route 1 or route 2 depending on the positive or negative quotation of the congruence indicator.

In an alternative, the directing of the method through Route 1 (congruence indicator is positive (+), the reply to the congruency recognition is "YES"), Route 2 (congruence indicator is negative (−) or neutral (0), the reply to the congruency recognition is "NO") or through Route 3 (congruence indicator "(?)" not clearly established) intervenes after the step S30 (where the congruency indicator is determined). In that situation, the step S40 of displaying a sign representative of the congruence indicator, at least for the positive congruency indicator (+), and if allowed by the system also for the negative congruency indicator (−) and the neutral congruency indicator (0), is implemented after the directing towards Route 1 or Route 2 or Route 3.

Figure 4:
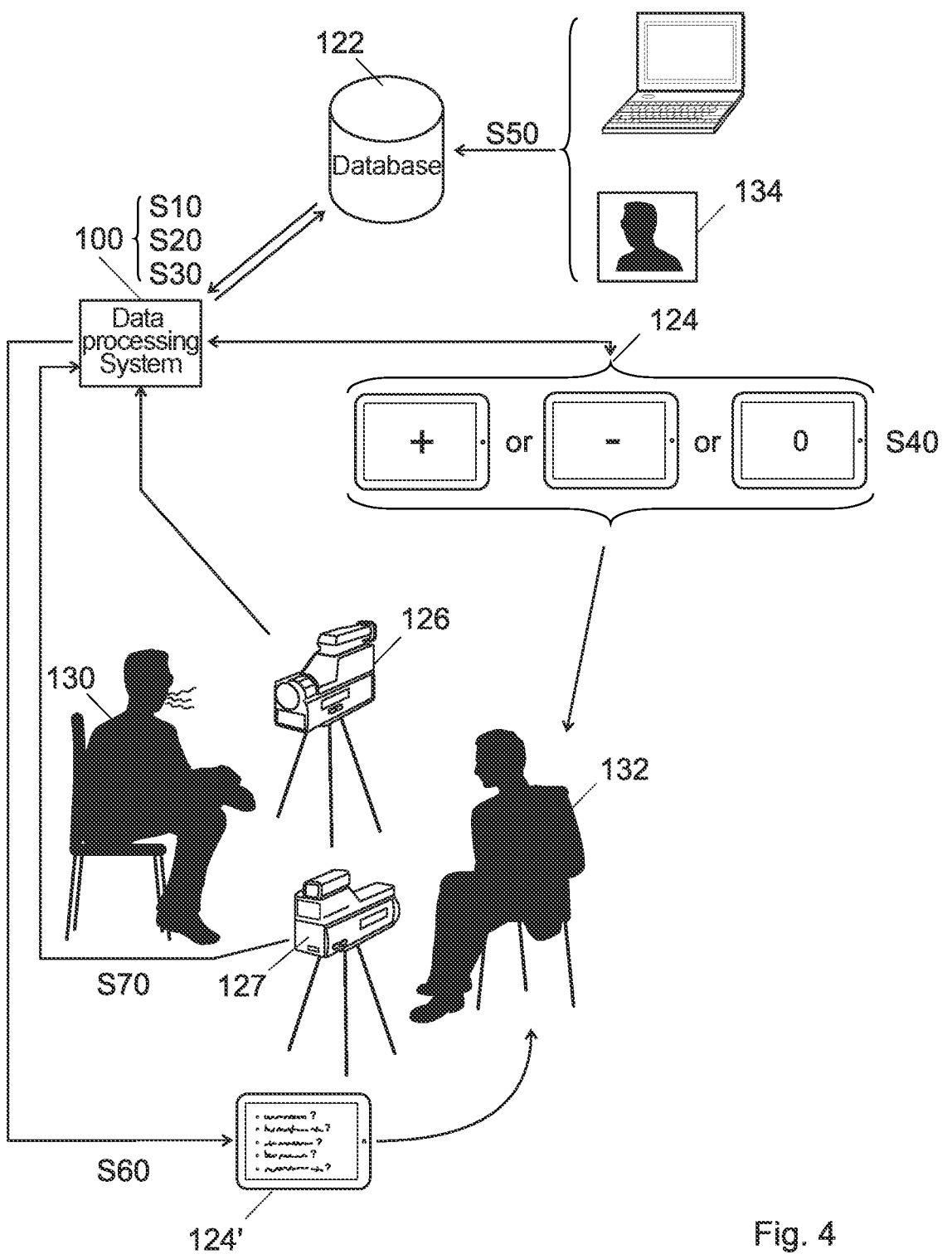
FIG. 4 is another representation of a method and of a system for providing indicators of congruence or incongruence between the body language and the Speech of a person which can be implemented in an embodiment of the system according to the present invention.

As can be seen from FIG. 4, the person or subject 130 whose Speech will be analysed (for instance the interviewee 130) according to the invention is placed facing the video recording device 126. Such a video recording device 126 can be for instance a video camera. This video recording device 126 allows to capture video sequences comprising both audio sequences (audio signal captured by a microphone or equivalent) and visual sequences (series of images captured by image capturing device). Such a video recording device 126 can be a hand-held device, or can be integrated into another system such as glasses, contact lens or other types of devices. This video recording device 126 is placed such that the face and the body of the subject 130 can be both video recorded.

The interviewer 132 is preferably placed facing the subject 130 for a better discussion comfort as shown in FIG. 4, but it is not necessary. Alternatively, the interviewer 132 and the interviewee 130 are communicating live with each other via telecommunication devices equipped with screen, camera and microphone, such as a computer facing the interviewee 130 and another computer facing the interviewer 132: in that situation, the interviewee 130 and the interviewer 132 can have the exchanges described in the present text through Internet using an application such as but not limited to Whatsapp, Skype, Zoom . . . . The interviewer 132 has access to a display 124 for receiving information from the system 100 (step 40), among which a congruence indicator (+ for positive, − for negative or 0 for neutral on FIG. 4).

In a possible embodiment, the interviewer 132 has also access to another display 124' (see FIG. 4) which provides a series of formulations of hypotheses (notably affirmations or questions) provided by the system 100, and notably based on said indicator of congruence or of incongruence of the previously analysed video sequence. This series of formulations of hypotheses can alternatively be shown on the same display 124 as the congruency indicator, or through any other device, notably any other display device, including but not limited to glasses. This step corresponds to S60 in FIG. 3. This series of hypotheses are helpful especially when the congruence indicator is negative, in order to check (confirm or infirm) the incongruence of the reply of the interviewee 130 regarding the item (information, theme, topic) of the previously analysed video sequence. In that situation, one of the hypotheses is chosen by the interviewer 132 and is used and voiced in presence of the subject 130, and the subject response is being simultaneously recorded and creating another video sequence of the subject, for a further analyse. Alternatively, instead of formulating the list of hypotheses (or list of questions or list of questions+hypotheses) on a display 124' as shown on FIG. 3, in an alternative embodiment, this list is proposed by an avatar speaking to the interviewer 132. This could be implemented alternatively through an audio signal transmitted to the interviewer 132 by an earpiece, glasses or any other audio device.

In an embodiment there is only one video recording device 126 as previously described. In another embodiment, the system further comprise a second video recording device 127 as shown on FIG. 4. This second video recording device 127 is for example a second camera and is used to capture another video of the interviewer 132. This second video recording device 127 capture video sequences comprising both audio sequences (audio signal captured by a microphone or equivalent) and visual sequences (series of images captured by image capturing device). In a variant, which is possible when the two (or more) persons/speakers are physically located in the same room, this second video recording device 127 has no microphone (or such a microphone or equivalent is shut off) and only capture visual sequences: in this case, the system can use the audio sequence of the first video recording device 126 to separate the voice/speech of the interviewer 132 from the speech/voice of the interviewee 130 (which is called diarization).

Also, when using at the same time a first video recording device 126 and a second video recording device 127, preferably the first video recording device 126 is facing the interviewee 130 and the second video recording device 127 is facing the interviewer 132 as shown in FIG. 4. In an alternative embodiment not shown, the two persons (such as the interviewee 130 and the interviewer 132, but any other possible situation of Speech with at least two persons/speakers) are not located in the same room and are each facing a video recording device included in a computer or any other telecommunication devices equipped with screen, camera and microphone and allowing the two (or more than two) persons to communicate live with each other. With such a second video recording device 127, the system can also perform recognition of what is called "perception management", namely in the present case the influence of the behaviour and Speech/questions of the interviewer 132 on the Speech of the interviewee. In other words, by having the sequences of images and audio signals of both people (interviewer 132 or interviewee 130), in addition to the analysis of the different clues (visual cues and Audio cues) to establish congruence or incongruence, the system can be used to detect evidence of this scientific theory known as "perception management" stipulating that the attitude, behaviour, thoughts of one person towards the other, influences the behaviour of the other person and vice versa. It has been shown by scientific research (Vrij) that the simple fact of thinking the person in front of us is "guilty" changes his behaviour. In the same way, the interviewee 130 can change the behaviour of the interviewer 132 through his or her attitude. Thus, by installing two cameras, one filming the interviewee 130 and the other filming the interviewer 132, the system will be able to highlight the behaviours of the interviewer that influence the other's attitude (interviewee's attitude) by detecting and analysing the different clues (visual cues and Audio cues) of both interviewee 130 and interviewer 132. In other words, observing a person during an interview (which is particularly relevant with a video recording device) can influence the behaviour of this person. Also, the interviewee 130 can use perception management to influence the interviewer 132. Perception management is both verbal and non-verbal. Actually, our role, our ornaments, our attitude (intentional or unconscious) affects others. The objective is to influence the observation of the other person in an exchange between two persons. For example, you may yawn excessively as if you were bored or squatting on a couch, stretch your arms, take up space, etc. Audio signals can be used through standard sentences: "I could never hurt anyone," "You don't think that about me, do you?", and/or in the case of the raising of the voice. All these signals, verbal signals and non-verbal signals, should alert the interviewer 132 and give him also Visual cues or Audio cues. Verbal signals (Audio cues) and non-verbal signals (Visual cues) will also be analyzed by the system, in the course of the method, in order to establish perception management through indicator of perception management represented by a visual sign (such as the displaying of an icon and/or the displaying of a colour on a screen) or by an audio signal (that can be displayed in an earpiece or through another audio equipment). If those signals are detected as forming a neutral indicator of perception management (or neutral influence indicator) they will be signaled (both to the interviewer and to the interviewee or only to one person, according to each one's needs) for instance by an orange colour (or by an neutral audio signal); if those signals are intrusive (detection of an influence of the Speech of one of the two persons on the Speech of the other of the two persons, and/or inversely) then an indicator of intrusive perception management (or negative influence indicator) be signaled for instance by a red colour (or by an intrusive audio signal), and if those signals are detected as non-intrusive (detection of no influence of the Speech of one of the two persons on the Speech of the other of the two persons, and/or inversely), then an indicator of non-intrusive perception management (or positive influence indicator) is signaled for instance in green (or by an non-intrusive audio signal).

By using two video recording devices 126 and 127 and by analyzing the data collected from the two persons involved in the exchange during the Speech, the system and the method can also bring some valuable inputs to complete and refine this theory of perception management, either for determining the influence of the first person on the (other) second person, or for determining the influence of the (other) second person on the first person or for determining both the influence of the first person on the (other) second person and the influence of the first person on the (other) second person.

This analysis of the influence of the behaviour and Speech of the Interviewer 132 on the interviewee 130 (and inversely) can also be used the system 100 to provide the series of formulations of hypotheses (notably affirmations or questions) to the display 124' (or 124), in order to confirm or infirm whether the congruence or absence of congruency detected is maintained when changing the behaviour and/or the Speech of the Interviewer 132 (interviewee 130). In that situation, the system 100 proposes some lists of hypotheses to the user (Interviewer 132) so that he/she can confirm or infirm the previously perceived clues (detected Visual cues or Audio cues). This is a finer analysis than using only direct determination of the congruence indicator with the detected Visual cues or Audio cues. Indeed, it is useful and meaningful to identify the incongruence or congruence from detected Visual cues or Audio cues, but it is important to go further, especially when this indicator of congruence is not a positive indicator of congruence, and in particular when this indicator of congruence is a negative indicator of congruence, and validate this congruency indicator of the person who holds alone the reality of what he or she has felt. In this sense, the validation of the incongruency (or congruency or neutral indicator of congruence), also known as TH (Test of Hypothesis, which formulates hypotheses to recreate the emotional state and the experienced feeling) following a behavioural interview, makes it possible to recreate the internal state experienced by the person at the time of the incongruence and confirm or not this incongruence, by confirming or infirming the preceding detected clues (Visual cues and/or Audio cues).

The system according to the invention can therefore relates the visual cues to the audio cues according to their rating. If an incongruence is reported, the Interviewer 132 will be offered hypotheses to apply the TH method. This step corresponds to S60 in FIG. 3. According to studies from which the TH method derives, the paleo limbal pole of the brain is the honest part. This means that the body reacts according to its animal part and thus delivers so-called sincere visual signals. Indeed, these are very fast reactions and do not pass through the neolimbic cortex pole which can "think" and thus want to condition his speech. The premise of the TH method is that when a person listens to a hypothesis/story He/she does not speak, but his/her body gives us signals. Indeed, without passing through the neo-limbal cortex pole, the signal given will arrive from the paleo limbal pole and will thus be honest. Thus, when a hypothesis is stated, the observed signal will confirm or not the detected incongruence.

The TH method was implemented following the under-standing of the different poles of the brain. Indeed, depend-ing on which one is most active, the type of cues will not be the same. Reptilian/paleolimbic brains are considered in congruence as being "honest". It includes, among other things, clues/cues related to feeled emotions and to survival strategies (3F). In the analysis of congruence, the neolimbic cortex brain concerns words. The neolimbic cortex brain is considered to be the "lying" brain in the field of profiling. On another side, the prefrontal cortex is adaptive, therefore the one where our full potential and cues such as comfort and isopraxia are located.

This means that the body reacts according to its animal part and thus delivers so-called sincere, honest visual signals (visual cues). Indeed, these are very fast reactions which do not pass through the neolimbic pole of the cortex which can "think" and therefore is able to condition/adapt its speech. The premise of the TH method is that when a person is listening to an hypothesis or a story, he (she) does not speak, but his(her) body gives us signals (visual Cues of the body language). Indeed, without passing through the neolimbic cortex pole, the given signal(s) will arrive from the reptilian/paleolimbic pole and is(are) therefore honest. Thus, when a hypothesis is formulated, the observed signal (visual Cues of the body language) will confirm or not the incongruity detected in a previous cycle of steps S10, S20 and S30.

In a possible embodiment of the system and of the method described in the present text, the Speech of the person 130 takes place in front of another person considered as an interviewer 132, so that the Speech forms an interview between said person or interviewee 130 and an interviewer 132.

In a first variant, the method further comprises the fol-lowing steps:

f/ providing a second video recording device 127 adapted to record images of said interviewer 132 including face and at least some parts of the body, g/ recording also a video of the Speech of that interviewer 132 with said second video recording device 127, said video being divided into n video sequences comprising n sequences of images (or n visual sequences) and n corresponding audio sequences, h/ detecting at least one Visual cue Vc of the interviewer 132 for each sequence of images and detecting at least one Audio cue Ac of the interviewer 132 for each audio sequence, i/ for each video sequence, analysing the rating of the Audio cue Ac and of the Visual cue Vc of the person forming the interviewee 130 with respect to the Visual cue Vc and Audio cue Ac of the interviewer 132, whereby establishing a positive or negative influence indicator, whereby the influence indicator is positive when there is a detected influence of the Visual cue Vc and Audio cue Ac of the interviewer 132 on the rating of the Audio cue Ac and of the Visual cue Vc of the person forming the interviewee 130, and where the influence indicator is negative when there is no detected influence of the Visual cue Vc and Audio cue Ac of the interviewer on the rating of the Audio cue Ac and of the Visual cue Vc of the person forming the interviewee 130.

In other cases, when it is not clearly detected whether there is or not an influence of the Visual cue Vc and Audio cue Ac of the interviewer 132 on the rating of the Audio cue Ac and of the Visual cue Vc of the person forming the interviewee 130, a neutral influence indicator is established.

In a second variant, the method further comprises the following steps:

f/ providing a second video recording device adapted to record images of said interviewer including face and at least some parts of the body, g/ recording also a video of the Speech of that interviewer with said second video recording device, said video being divided into n video sequences comprising n sequences of images (or n visual sequences) and n corresponding audio sequences, h/ detecting at least one Visual cue Vc of the interviewer for each sequence of images and detecting at least one Audio cue Ac of the interviewer for each audio sequence, i/ for each video sequence, analysing the rating of the Audio cue Ac and of the Visual cue Vc of the person forming the interviewer with respect to the Visual cue Vc and Audio cue Ac of the interviewee (130), whereby establishing a positive or negative influence indicator, whereby the influence indicator is positive when there is a detected influence of the Visual cue Vc and Audio cue Ac of the interviewee on the rating of the Audio cue Ac and of the Visual cue Vc of the person forming the interviewer (132), and where the influence indicator is negative when there is no detected influence of the Visual cue Vc and Audio cue Ac of the interviewee interviewer on the rating of the Audio cue Ac and of the Visual cue Vc of the person forming the interviewer (132).

By highlighting, namely detecting, the different audio and visual signals of both interviewee and interviewer, the system is also able to give feedback to the interviewer 132 about the body language of the interviewee 130.

In that situation, in a possible embodiment, said detected influence indicator is used to provide to the interviewer 132 a series of formulations of hypotheses in the form of affirmations and/or questions.

Figure 5:
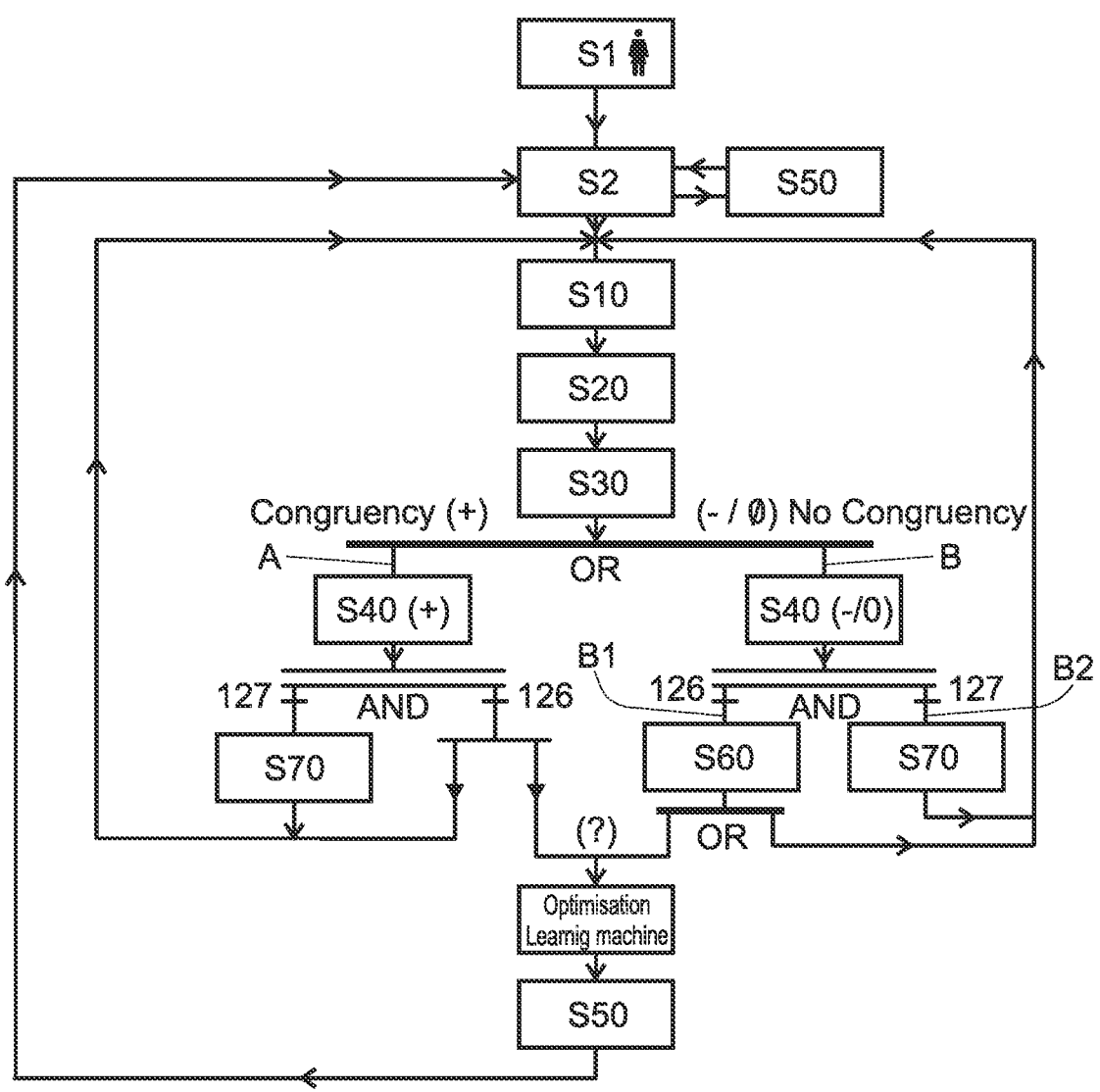
FIG. 5 shows another method for providing indicators of congruence or incongruence between the body language and the Speech of a person which can be implemented in an embodiment of the system according to the present invention.

FIG. 5 shows another method according to the invention for providing indicators of congruence or incongruence between the body language and the Speech of a person, which uses the perception management in a step S70 con-sidering the video sequences of the interviewer 132 captured by the second video recording device 127.

In that respect, Steps S1, S2, S10, S20, S30 and S40 are the same as those previously described in relation with FIG. 3. Then, two routes A and B are possible at the moment of the displaying step S40 or after the displaying step S40 depend-ing of the congruence indicator:

Route A: if the congruence indicator is positive (on the left of FIG. 5); then the video sequences (sequences of images and audio signals) of both people (interviewer 132 or interviewee 130) recorded by the first video recording device 126 and by the second video record-ing device 127 are used by the system to detect whether there is an influence of the behaviour and Speech/questions of the interviewer 132 on the Speech of the interviewee 130 (step 70 of perception management), and then the method/system makes a loop back to step S10 in order to evaluate the congruence or incongruence of the Speech of the interviewee 130 for another video sequence;

Route B: if the congruence indicator is negative(–) or neutral (0) (on the right of FIG. 5); then the video sequences (sequences of images and audio signals) of both people (interviewer 132 or interviewee 130) recorded by the first video recording device 126 and by the second video recording device 127 are used by the system to implement both following steps:

subroute B1: proposing a list of hypothesis in the form of a list of affirmations and/or of questions based on said indicator of congruence or of incongruence of the previously analysed video sequence (step S60 of Hypothesis Proposal), and then the method/system makes a loop back to step S10 in order to evaluate the congruence or incongruence of the Speech of the interviewee 130 for another video sequence, and subroute B2: detect whether there is an influence of the behaviour and Speech/questions of the interviewer 132 on the Speech of the interviewee 130 (step S70 of perception management), and then the method/system makes a loop back to step S10 in order to evaluate the congruence or incongruence of the Speech of the interviewee 130 for another video sequence.

In parallel to possible routes A and B, if the incongruence indicator resulting from the video sequence captured by the first recording device 126 is not clearly established (see "(?)" on the center end bottom of FIG. 5), then for an optimisation step of the learning machine, in step S50 there is an expert adjustment, which correspond to the human verification and possible correction by an expert 134 of the congruence indicator, which further step of congruence indicator also possibly serves to train further the self-learning machine 120. Then, the method follows previously described steps starting from step S10.

The systems and methods according to the invention take into account all the component of the human behaviour, namely from micro-expression to pacification gestures.

The data processing system 100 of FIG. 1 may be located and/or otherwise operate at any node of a computer network, that may exemplarily comprise clients, servers, etc., and it is not illustrated in the figure. In the embodiment illustrated in FIG. 1, the system 100 includes communication network 102, which provides communications between processor unit 104, memory 106, visual cues detector 108, communications unit 110, input/output (I/O) unit 112, and audio cues detector 114.

Processor unit 104 serves to execute instructions for software that may be loaded into memory 106. Processor unit 104 may be a set of one or more processors or may be a multi-processor core, depending on the particular implementation. Further, processor unit 104 may be implemented using one or more heterogeneous processor systems in which a main processor is present with secondary processors on a single chip. As another illustrative example, the processor unit 104 may be a symmetric multiprocessor system containing multiple processors of the same type.

In some embodiments, the memory 106 shown in FIG. 1 may be a random access memory or any other suitable volatile or non-volatile storage device. The database 122 connected to the communication unit 110 can be a persistent storage that may take various forms depending on the particular implementation. For example, such a persistent storage may contain one or more components or devices. Such a persistent storage may be a hard drive, a flash memory, a rewritable optical disc, a rewritable magnetic tape, or some combination of the above. The media used by such a persistent storage may also be removable such as, but not limited to, a removable hard drive.

The communications unit 110 shown in FIG. 1 provides for communications with other data processing systems or devices. In these examples, communications unit 110 is a network interface card. Modems, cable modem and Ethernet cards are just a few of the currently available types of network interface adapters. Communications unit 110 may provide communications using either or both physical and wireless communications links.

The input/output unit 112 shown in FIG. 1 enables input and output of data with other devices that may be connected to the data processing system 100. In some embodiments, input/output unit 112 may provide a connection for user input through a keyboard and mouse. Further, input/output unit 112 may send output to a printer. Display 124 (and display 124') provide(s) a mechanism to display information to a user, for instance a tablet computer or a smartphone.

Instructions for the operating system and applications or programs can be located on the persistent storage. These instructions may be loaded into the memory 106 for execution by processor unit 104. The processes of the different embodiments may be performed by processor unit 104 using computer implemented instructions, which may be located in a memory, such as memory 106. These instructions are referred to as program code, computer usable program code, or computer-readable program code that may be read and executed by a processor in processor unit 104. The program code in the different embodiments may be embodied on different physical or tangible computer readable media, such as memory 106 or persistent storage.

Program code 116 can be located in a functional form on the computer-readable media 118 that is selectively removable and may be loaded onto or transferred to the system 100 for execution by processor unit 104. Program code 116 and computer-readable media 118 form a computer program product in these examples. In one example, the computer-readable media 118 may be in a tangible form, such as, for example, an optical or magnetic disc that is inserted or placed into a drive or other device that is part of persistent storage (database 122) for transfer onto a storage device, such as a hard drive that is part of persistent storage 108. In a tangible form, the computer-readable media 118 also may take the form of a persistent storage, such as a hard drive, a thumb drive, or a flash memory that is connected to the system 100. The tangible form of computer-readable media 118 is also referred to as computer recordable storage media. In some instances, computer-readable media 118 may not be removable.

Alternatively, the program code 116 may be transferred to the system 100 from computer-readable media 118 through a communication link to communications unit 110 and/or through a connection to input/output unit 112. The communications link and/or the connection may be physical or wireless in the illustrative examples. The computer-readable media may also take the form of non-tangible media, such as communications links or wireless transmissions containing the program code.

The different components illustrated for data processing system 100 are not meant to provide architectural limitations to the manner in which different embodiments may be implemented. The different illustrative embodiments may be implemented in a data processing system including components in addition to or in place of those illustrated for data processing system 100. Other components shown in FIG. 1 can be varied from the illustrative examples shown. For example, a storage device in the system 100 (and/or in the self-learning machine 120) is any hardware apparatus that may store data. Memory 106, persistent storage, and computer-readable media 118 are examples of storage devices in a tangible form.

The transfer of data between the different parts of the data processing system 100 is possible via the communication system 102. This communication system 102 can be totally or partially wireless, or totally or partially wired. A wireless communication network or part of the communication network can be for instance based on Wi-fi technology. A wired communication network or part of the communication network can be for instance formed by a data bus system or any other fixed communication network. Also the communication between the data processing system 100 and any of or several of the database 122, self-learning machine 120, display 124, display 124', computer reading media 118, and the video recording device, can be implemented using only a wireless communication network (such as Wi-fi) or using only a wired communication network (such as data bus system), or using partially a wireless communication network (such as Wi-fi) and partially a wired communication network (such as data bus system).

In a non-limitative way, the self-learning machine 120 comprises a neural network, for instance a convolution neural network, and/or a deep learning neural network. According to an embodiment, said self-learning machine is a deep learning machine.

The display 124 for receiving information from the system 100 and the other display 124' which provides a series of formulations of hypotheses provided by the system 100 are shown in FIG. 4 as screens of a tablet computer, but they can be replaced by other displays such as screen of a tablet or screens of another device, such as a hand-held device, or these displays can be integrated into another system such as glasses, contact lens or another type of device. These displays 124 and 124' give a visual feedback (visual signal) to the interviewer 132 (user of the system 100) but this visual signal can also be replaced by or cumulated with (an)other type(s) of signal(s), such as an audio signal, and/or a vibrating signal, including via an earphone or an device worn on the body (for instance a watch or a bracelet or an earring or a pendant . . . ).

Another aspect of the invention is a training method proposed for training a self-learning machine 120, such as a neuronal network, in order to determine indicators of congruence or incongruence between the body language and the Speech of a person or between the cues themselves, comprising:

a) Collecting an input dataset including:
approved data of a collection of analysed Speech of persons, said approved data comprising for each analysed Speech:
a set of sequences, comprising audio sequences and video sequences, each audio sequence corresponding to one video sequence
for each sequence, a pair or a group of identified cues including at least one Audio cue Ac identified from the audio sequence of said sequence, and at least one Visual cue Vc identified from the corresponding video sequence of said sequence, and
For each pair or group of identified cues, a congruence indicator approved by an expert 134, forming thereby an approved congruence indicator for said sequence, b) Training the self-learning machine with said input dataset As previously explained, this congruence indicator or approved congruence indicator can be a positive congruence, a negative congruence indicator, or a neutral congruence indicator. In an embodiment, this congruence indicator or approved congruence indicator results from a video of a Speech of that person, wherein said video is divided into n video sequences comprising n sequences of images (or n visual sequences) and n corresponding audio sequences, wherein for each sequence of images, at least one Visual cue Vc is detected and attributed at least one rating among positive Vc+, neutral Vc0 or negative Vc, wherein for each audio sequence, at least one Audio cue Ac is detected and attributed at least one rating among positive Ac+, neutral Ac0 or negative Ac, and wherein for each video sequence, the rating of said Audio cue Ac is compared with the rating of said Visual cue Vc, thereby giving a congruence indicator which is a positive congruence indicator if both ratings are either positive (Vc+ and Ac+) or negative (Vc+ and Ac+), a negative congruence indicator if one of the ratings is positive and the other one is negative (Vc+ and Ac−, or Vc− and Ac+), and a neutral congruence indicator if one of the ratings is neutral (Vc0 or Ac0).

In an embodiment, for determining an approved congruence indicator, a sign of discomfort, a sign of comfort and/or a pacificator sign is (are) also determined and used.

In an embodiment, when detecting in a video sequence an Audio cue or an Visual cue, among possible cues are possibly included a sign of discomfort, a sign of comfort or a pacificator sign, those signs being possibly a visual sign or an audio sign.

More generally, the invention also concerns a method for training a self-learning machine, such as a neural network, in order to determine congruence or incongruence between the body language and the oral part of the Speech of a person comprising the following steps:

a) providing a self-learning machine, such as a neural network, arranged for receiving as input an input dataset including:
approved data of a collection of analysed Speeches of persons, said approved data comprising for each analysed Speech:
a set of video sequences, comprising audio sequences and visual sequences, each audio sequence corresponding to one visual sequence, and
For each video sequence, an approved congruence indicator for said video sequence,
b) Training the self-learning machine with said input dataset.

The invention also concerns a data processing system for determining congruence or incongruence (establish a congruence rate) between the body language and the Speech of a person, comprising a self-learning machine, such as a neural network, arranged for receiving as input a dataset including:
approved data of a collection of analysed Speeches of persons, said approved data comprising for each analysed Speech:
a set of video sequences, comprising audio sequences and visual sequences, each audio sequence corresponding to one visual sequence, and
an approved congruence indicator for each of said video sequence
said self-learning machine being trained so that the data processing system is able to deliver as output a congruence indicator. Such a congruence indicator is delivered by the data processing system after the self-learning machine has been trained and has received as input another video sequence comprising an audio sequence and the corresponding visual sequence.

In an embodiment of the method (system), said data set further includes for each sequence, a pair or a group of identified cues including at least one Audio cue Ac identified from the audio sequence of said sequence, and at least one Visual cue Vc identified from the corresponding visual sequence of said video sequence, said identified Audio cue Ac and said identified Visual cue Vc forming a pair of identified cues, and for each pair or group of identified cues, said data set further includes said approved congruence indicator, the latter be possibly a congruence indicator approved by an expert 134.

REFERENCE NUMBERS USED IN THE FIGURES

S1 Collecting input step
S2 Training step
S10 Cues detection
S20 Cues rating
S30 Congruency determination
S40 Displaying
S50 Expert adjustment
S60 Hypothesis Proposal
S70 Perception management
100 Data processing System
102 Communication system (Data bus system)
104 Processing unit
106 Memory
108 Visual Cues Detector
110 Communication unit
112 I/O unit
114 Audio Cues Detector
116 Program code
118 Computer readable media
120 Self-learning machine
122 Database (with persistent storage)
124 Display receiving information from the system 100
124' Display providing a series of formulations of hypotheses
126 Video recording device (such as for example a video camera)
127 Second video recording device (such as for example a video camera)
130 Person (subject or interviewee)
132 Interviewer
134 Expert

The invention claimed is:

1. Method for providing indicators of congruence or incongruence between the body language and the Speech of a person comprising the following steps:
a) providing a video recording device adapted to record images of a subject including face and at least some parts of the body,
b) recording a video of the Speech of that person with said video recording device, said video being divided into n video sequences comprising n sequences of images and n corresponding audio sequences,
c) for each sequence of images, detecting at least one Visual cue Vc and attributing at least one rating among positive Vc+, neutral Vc0 or negative Vc− for each visual cue Vc, d) for each audio sequence, detecting at least one Audio cue Ac and attributing at least one rating among positive Act, neutral Ac0 or negative Ac− for each Audio cue Ac,
e) for each video sequence, comparing the rating of said Audio cue Ac with the rating of said Visual cue Vc, and giving a congruence indicator which is a positive congruence indicator if both ratings are either positive (Vc+ and Ac+) or negative (Vc+ and Ac+), a negative congruence indicator if one of the ratings is positive and the other one is negative (Vc+ and Ac−, or Vc− and Ac+), and a neutral congruence indicator if one of the ratings is neutral (Vc0 or Ac0).

2. Method according to claim 1, wherein said Visual cue Vc is one of the following: all facial expressions or body language cues, including a visual sign of discomfort, a visual sign of comfort or a visual pacificator sign.

3. Method according to f claim 1, wherein said Audio cue Ac is one of the following: for the voice: rhythm, speed, high volume, low volume, pitch, high ton, low ton; for the negative or positive emotional voice; verbal style: linguistics, inquiry, word, count, change of verbal style and a positive or negative sentiment expressed in the audio sequence, an audio sign of discomfort, an audio sign of comfort and an audio pacificator sign.

4. Method according to claim 1, further comprising a reference table with the rating correspondence(s) of the Visual cue Vc and of the Audio cue Ac.

5. Method according to claim 1, wherein it further comprises before step b), a preliminary step b0) for baseline establishment during the following sub-steps are implemented:
i) a reference film is shown to said person, said reference film comprising m reference film sequences, at least some of the reference film sequences being emotionally charged;
ii) during the showing of the film, a recording of a reference video of the person is done;
iii) dividing the reference video into m reference video sequences, each reference video sequence corresponds to a reference film sequence of said film;
iv) for each reference video sequence, detecting at least one Visual cue Vc of a micro expression that is memorised in a baseline table of said person.

6. A method according to claim 1, wherein the Speech of the person takes place in front of another person considered as an interviewer, so that the Speech forms an interview between said person or interviewee and an interviewer, wherein the method further comprising the following steps:
f) providing a second video recording device adapted to record images of said interviewer including face and at least some parts of the body,
g) recording also a video of the Speech of that interviewer with said second video recording device, said video being divided into n video sequences comprising n sequences of images and n corresponding audio sequences,
h) detecting at least one Visual cue Vc of the interviewer for each sequence of images and detecting at least one Audio cue Ac of the interviewer for each audio sequence,
i) for each video sequence, analysing the rating of the Audio cue Ac and of the Visual cue Vc of the person forming the interviewee with respect to the Visual cue Vc and Audio cue Ac of the interviewer, whereby establishing a positive or negative influence indicator, whereby the influence indicator is positive when there is a detected influence of the Visual cue Vc and Audio cue Ac of the interviewer on the rating of the Audio cue Ac and of the Visual cue Vc of the person forming the interviewee, and where the influence indicator is negative when there is no detected influence of the Visual cue Vc and Audio cue Ac of the interviewer on the rating of the Audio cue Ac and of the Visual cue Vc of the person forming the interviewee.

7. A method according to claim 1, wherein said detected influence indicator is used to provide to the interviewer a series of formulations of hypotheses in the form of affirmations and/or questions.

8. A method according to claim 1, wherein the Speech of the person takes place in front of another person considered as an interviewer, so that the Speech forms an interview between said person or interviewee and an interviewer, wherein the method further comprising the following steps:

f) providing a second video recording device adapted to record images of said interviewer including face and at least some parts of the body, g) recording also a video of the Speech of that interviewer with said second video recording device, said video being divided into n video sequences comprising n sequences of images and n corresponding audio sequences, h) detecting at least one Visual cue Vc of the interviewer for each sequence of images and detecting at least one Audio cue Ac of the interviewer for each audio sequence, i) for each video sequence, analysing the rating of the Audio cue Ac and of the Visual cue Vc of the person forming the interviewer with respect to the Visual cue Vc and Audio cue Ac of the interviewee, whereby establishing a positive or negative influence indicator, whereby the influence indicator is positive when there is a detected influence of the Visual cue Vc and Audio cue Ac of the interviewee on the rating of the Audio cue Ac and of the Visual cue Vc of the person forming the interviewer, and where the influence indicator is negative when there is no detected influence of the Visual cue Vc and Audio cue Ac of the interviewee interviewer on the rating of the Audio cue Ac and of the Visual cue Vc of the person forming the interviewer.

9. System for providing indicators of congruence or incongruence between the body language and a person's Speech, comprising:

a self-learning machine programmed to receive as input, on the one hand, several sets of audio sequences of a person's Speech, wherein each audio sequence corresponds to one Audio cue Ac and, on the other hand, a set of sequences of images of said person during said Speech, wherein said images comprising face and at least some parts of the body and wherein each sequence of images corresponds to one Visual cue Vc, the said self-learning machine having been trained so that said system is able to deliver as output, after analysing a video sequence comprising one sequence of images and one corresponding audio sequence, with both at least one identified Visual cue Vc based on said sequence of images and at least one identified Audio cue Ac based on said audio sequence, which forms a pair or a group of identified cues (Vc+Ac) and points to a congruence or incongruence, wherein for each Audio cue Ac and each Visual cue Vc, attributing at least one rating among positive rating, neutral rating, or negative rating.

10. System according to claim 9, wherein said Visual cue Vc is either a facial expression or a body language cue.

11. System according to claim 10, wherein said system further comprises a Visual cue detector able to analyse said video sequences and to provide one or several corresponding identified Visual cues Vc.

12. System according to claim 10, wherein said system further comprises an Audio cue detector able to analyse said audio sequences and to provide one or several corresponding identified Audio cues Ac.

13. System according to claim 10, wherein said self-learning machine comprises a clustering or multi-output artificial neuronal network.

14. System according to claim 10, wherein said self-learning machine comprises an artificial neuronal network with a multiplicity of layers.

15. System according to claim 10, wherein said self-learning machine is a deep learning machine.

16. System according to claim 10, wherein said self-learning machine will, with enough data, infer the best and most accurate cues that determine the congruence and incongruence between the Audio cues (Ac), Visual cues (Vc) and the cues themselves.

17. A system according to claim 9, wherein said Audio cue Ac comprises at least one of the following: voice, negative emotional voice, positive emotional voice and verbal style.

18. System according to claim 9, wherein said self-learning machine further receives as input a reference table with the rating correspondence of each of the Visual cues Vc and of each of the Audio cues Ac, and wherein based on said identified Visual cue Vc and on said identified Audio cue Ac of the analysed video sequence and based on said reference table, said system is further able to deliver as output both at least one Visual cue Vc rating and at least one Audio cue Ac rating, which forms a pair or a group of cue ratings.

19. System according to claim 18, wherein said system is further able through said pair or said group of cue ratings corresponding to the analysed video sequence, to deliver as output, an indicator of congruence or incongruence of the analysed video sequence.

20. System according to claim 19, wherein said indicator of congruence or of incongruence is a positive congruence indicator for the analysed video sequence when the Visual cue Vc rating and the Audio cue Ac rating are the same, and negative congruence indicator of the analysed video sequence when the Visual cue Vc rating and the Audio cue Ac rating are different and one of the rating is positive and the other one is negative, or the cue in itself displays a sign of incongruence or congruence.

21. System according to claim 19, wherein said indicator of congruence is a positive congruence indicator for the analysed video sequence when the Visual cue Vc rating and the Audio cue Ac rating are both either negative or positive.

22. System according to claim 21, wherein said system is further able, based on said indicator of congruence or of incongruence of the analysed video sequence, to provide a series of formulations of hypothesis, one being chosen manually and being used and voiced in presence of the subject, and the subject response is being simultaneously recorded and creating another video sequence of the subject.

23. System according to claim 19, wherein said indicator of congruence is a negative congruence indicator of the analysed video sequence is detected, when the Visual cue Vc rating and the Audio cue Ac rating are opposite and therefore one of the rating is positive and the other one is negative.

24. System according to claim 19, wherein said indicator of congruence or of incongruence is a positive congruence indicator for the analysed video sequence when the Visual cue Vc rating and the Audio cue Ac rating are the same, and negative congruence indicator of the analysed video sequence when the Visual cue Vc rating and the Audio cue Ac rating are different and one of the rating is positive and the other one is negative, or the cue in itself displays a sign of incongruence or congruence and wherein said indicator of congruence or of incongruence is a neutral congruence indicator if one of the rating is a neutral rating.

25. System according to claim 9, wherein said system further comprises a display, and wherein said indicators of congruence or of incongruence are displayed on said display with corresponding signs, and with information identifying the corresponding analysed video sequence.

26. System according to claim 25, wherein the corresponding signs include symbols, colours, vibrations, audio.

\* \* \* \* \*